United States Patent [19]
Gelman et al.

[11] Patent Number: 5,980,746
[45] Date of Patent: Nov. 9, 1999

[54] MEMBRANE AND METHODS OF PREPARING AND USING SAME

[75] Inventors: Charles Gelman, Ann Arbor, Mich.;
Peter Konstantin, Gulf Breeze, Fla.;
Wilfrid Klaus Wixwat, Pensacola, Fla.;
Yujing Yang, Pensacola, Fla.;
Chung-Jen Hou, Pensacola, Fla.

[73] Assignee: Pall Corporation, East Hills, N.Y.

[21] Appl. No.: 08/966,261

[22] Filed: Nov. 7, 1997

Related U.S. Application Data

[63] Continuation-in-part of application No. 08/748,711, Nov. 14, 1996, abandoned.

[51] Int. Cl.$^6$ .............................. B01D 39/18; B01D 71/10
[52] U.S. Cl. ................................ 210/500.29; 210/500.27; 210/500.41; 428/308.8
[58] Field of Search ....................... 210/500.29, 500.27, 210/500.3, 500.31, 500.32, 500.41; 428/308.8, 304.4

[56] References Cited

U.S. PATENT DOCUMENTS

| | | |
|---|---|---|
| 3,876,738 | 4/1975 | Marinaccio et al. . |
| 4,340,479 | 7/1982 | Pall . |
| 4,374,232 | 2/1983 | Davis . |
| 4,466,931 | 8/1984 | Tanny . |
| 4,473,474 | 9/1984 | Ostreicher et al. . |
| 4,601,828 | 7/1986 | Gershoni . |
| 4,629,563 | 12/1986 | Wrasidlo . |
| 4,673,504 | 6/1987 | Ostreicher et al. . |
| 4,708,803 | 11/1987 | Ostreicher et al. . |
| 4,711,793 | 12/1987 | Ostreicher et al. . |
| 4,900,499 | 2/1990 | Mills . |
| 4,964,490 | 10/1990 | Watanabe . |
| 5,108,607 | 4/1992 | Kraus et al. . |
| 5,120,440 | 6/1992 | Nemoto ........................ 210/500.29 X |
| 5,209,849 | 5/1993 | Hu et al. ................................. 210/490 |
| 5,228,994 | 7/1993 | Tkacik et al. ................. 210/500.29 X |

FOREIGN PATENT DOCUMENTS

| | | |
|---|---|---|
| 0036315 | 9/1981 | European Pat. Off. . |
| 0036947 | 10/1981 | European Pat. Off. . |
| 0165077 | 12/1985 | European Pat. Off. . |
| 0228072 | 7/1987 | European Pat. Off. . |
| 0 257 635 | 3/1988 | European Pat. Off. . |
| 0 272 842 | 6/1988 | European Pat. Off. . |
| 0 280 560 | 8/1988 | European Pat. Off. . |
| 0 402 196 | 12/1990 | European Pat. Off. . |
| 0250137 | 8/1992 | European Pat. Off. . |
| 2651818 | 6/1977 | Germany . |
| 2829630 | 1/1979 | Germany . |
| 3327638 | 2/1985 | Germany . |
| 3342824 | 6/1985 | Germany . |
| 3701633 | 8/1988 | Germany . |
| 1295585 | 11/1972 | United Kingdom . |
| 1473857 | 5/1977 | United Kingdom . |
| 1495887 | 12/1977 | United Kingdom . |
| 2 081 604 | 2/1982 | United Kingdom . |
| WO 94/12040 | 6/1994 | WIPO . |

*Primary Examiner*—Daniel Zirker
*Attorney, Agent, or Firm*—Leydig, Voit & Mayer, Ltd.

[57] ABSTRACT

The present invention provides a membrane comprising (a) polymer solids comprising 60 wt. % or more of a fully synthetic organic polymer and optionally about 40 wt. % or less of a polymer of natural origin and (b) a cellulose compound which allows for the detection of a biological molecule of interest, wherein the cellulose compound is uniformly distributed throughout the surface of the membrane. The present invention also provides methods of preparing and using such membranes.

34 Claims, No Drawings

MEMBRANE AND METHODS OF PREPARING AND USING SAME

CROSS-REFERENCE TO RELATED APPLICATION

This patent application is a continuation-in-part of copending U.S. patent application Ser. No. 08/748,711, filed Nov. 14, 1996, abandoned.

TECHNICAL FIELD OF THE INVENTION

The present invention relates to a membrane suitable for use in immunodiagnostic assays and blotting assays and methods of preparing and using same.

BACKGROUND OF THE INVENTION

Membranes have become invaluable tools in both the clinical and experimental biotechnological arts. Specifically, membranes are integral to immunodiagnostic assays and a variety of blotting assays. However, currently available membranes possess qualities which limit their utility within the context of the foregoing applications.

Immunodiagnostic assays are generally performed by applying a test liquid containing antigens to a porous membrane containing antibodies. As the test liquid laterally diffuses through the membrane, antibodies will bind antigens to which they are directed with a high degree of specificity. The binding of the antibodies to the antigens serves as a detection means (e.g., the visualization of the presence of antigens), and the specificity with which antibodies bind to antigens allows for the determination of whether or not the test liquid contains specific antigens. Therefore, in immunodiagnostic assays, the membrane desirably possesses optimal immunodiagnostic properties. In other words, it is desirable that the membrane allow for optimal lateral diffusion of the test liquid, allow for adequate visualization of the existence of antigens in the test liquid (i.e., the membrane is capable of a high signal-to-noise ratio), allow for adequate protein binding, is hydrophilic, is capable of being uniformly manufactured in order to yield consistent results, and is safe to use.

Similarly, in a blotting assay, a membrane is contacted with a fluid comprising biological molecules such that the biological molecules become fixed to the membrane. Biological molecules of interest are subsequently visualized. It is desirable that the membrane utilized within the context of blotting assays have optimal blotting properties. Specifically, it is desirable that the membrane allow for the adequate binding of biological molecules, allow for adequate visualization of the biological molecules of interest (i.e., the membrane is capable of a high signal-to-noise ratio), is hydrophilic, is capable of being uniformly manufactured in order to yield consistent results, and is safe to use. However, unlike those membranes used in immunodiagnostic assays, blotting membranes need not allow for the lateral diffusion of biological molecules. In fact, for most blotting applications (e.g., southern blots, northern blots, western blots, and in situ hybridization of bacterial colonies), lateral diffusion is undesirable.

The most common types of membranes available for use in immunodiagnostic and blotting assays include polyvinylidenefluoride, nylon, and cellulose-based membranes (e.g., nitrocellulose and cellulose acetate membranes). Each of the membranes, however, possesses qualities which limit its utility in the foregoing applications. Nitrocellulose is prepared by the nitration of naturally occurring cellulose. During nitration, a broad distribution of heterogenous oligomeric and polymeric nitrated products is produced as a consequence of the partial acid digestion of cellulose. Exacerbating the problem is the fact that the purity of the cellulose starting material depends on its source and pre-nitration treatment. As a result, uniformity in the manufacture of nitrocellulose membranes is difficult to achieve. For similar reasons, it is also difficult to achieve uniformity in the manufacture of other cellulosic membranes, such as cellulose acetate membranes. Furthermore, nitrocellulose membranes present numerous laboratory safety concerns by virtue of their flammability and explosiveness. Cellulose acetate and nitrocellulose membranes are also disadvantageous in that such membranes are very brittle, easily broken, and difficult to wet.

Nylon and polyvinylidenefluoride membranes also have disadvantages associated with their use within the context of the foregoing applications. Nylon membranes strongly bind biological molecules and, consequently, have low signal-to-noise ratios. Polyvinylidenefluoride and other synthetic polymeric membranes cannot be used in applications where surface activity, which facilitates the binding of biological molecules, is necessary or where high lateral flow rates are necessary.

In view of the foregoing problems, there exists a need for membranes which can be used more effectively in immunodiagnostic and blotting assays. The present invention provides such a membrane and methods for the preparation thereof. These and other advantages of the present invention, as well as additional inventive features, will be apparent from the description of the invention provided herein.

BRIEF SUMMARY OF THE INVENTION

The present invention provides a membrane comprising (a) polymer solids comprising 60 wt. % or more of a fully synthetic organic polymer and optionally about 40 wt. % or less of a polymer of natural origin and (b) a cellulose compound which allows for the detection of a biological molecule of interest, wherein the cellulose compound is uniformly distributed throughout the surface of the membrane.

The present invention also provides methods of preparing such membranes. Specifically provided is a method of preparing a membrane comprising (a) selecting a base membrane comprising polymer solids, the polymer solids comprising 60 wt. % or more of a fully synthetic organic polymer and optionally about 40 wt. % or less of a polymer of natural origin, and (b) uniformly coating the base membrane with a coating solution, the coating solution comprising a cellulose compound which allows for the detection of a biological molecule of interest and a cellulose dissolving agent which is a solvent for the cellulose compound and is a non-solvent for the base membrane, to provide a membrane wherein the cellulose compound is uniformly distributed throughout the surface of the membrane. Also provided is a method of preparing a membrane comprising (a) admixing (i) polymer solids comprising 60 wt. % or more of a fully synthetic organic polymer and optionally about 40 wt. % or less of a polymer of natural origin and (ii) a cellulose compound, and (b) casting the admixture of step (a) to prepare a membrane wherein the cellulose compound is uniformly distributed throughout the surface of the membrane.

The present invention also provides a method of using a membrane to detect a biological molecule of interest comprising (a) contacting the membrane with a fluid comprising the biological molecule of interest and (b) detecting the biological molecule of interest on the membrane. Further provided is an immunodiagnostic assay kit comprising a membrane and a means for detecting a biological molecule of interest. Also provided is a blotting assay kit comprising a membrane and a blotting solution.

DESCRIPTION OF THE PREFERRED EMBODIMENTS

The invention may best be understood with reference to the following detailed description of the preferred embodiments. The present invention provides a membrane as well as methods for the preparation thereof. The present inventive membrane comprises (a) polymer solids comprising 60 wt. % or more of a fully synthetic organic polymer and optionally about 40 wt. % or less of a polymer of natural origin and (b) a cellulose compound which allows for the detection of a biological molecule of interest, wherein the cellulose compound is uniformly distributed throughout the surface of the membrane.

The first present inventive method of preparing a membrane comprises (a) selecting a base membrane comprising polymer solids, the polymer solids comprising 60 wt. % or more of a fully synthetic organic polymer and optionally about 40 wt. % or less of a polymer of natural origin, and (b) uniformly coating the base membrane with a coating solution, the coating solution comprising a cellulose compound which allows for the detection of a biological molecule of interest and a cellulose dissolving agent which is a solvent for the cellulose compound and is a non-solvent for the base membrane, to provide a membrane wherein the cellulose compound is uniformly distributed throughout the surface of the membrane. The second present inventive method of preparing a membrane comprises (a) admixing (i) polymer solids comprising 60 wt. % or more of a fully synthetic organic polymer and optionally about 40 wt. % or less of a polymer of natural origin and (ii) a cellulose compound, and (b) casting the admixture of step (a) to prepare a membrane wherein the cellulose compound is uniformly distributed throughout the surface of the membrane.

Polymer Solids

The polymer solids comprise a fully synthetic organic polymer and optionally a polymer of natural origin. The polymer solids preferably comprise 60 wt. % or more of a fully synthetic organic polymer and optionally about 40 wt. % or less of a polymer of natural origin; more preferably, 80 wt. % or more of a fully synthetic organic polymer and about 20 wt. % or less of a polymer of natural origin; even more preferably, 90 wt. % or more of a fully synthetic organic polymer and about 10 wt. % or less of a polymer of natural origin; and most preferably, 100 wt. % of a fully synthetic organic polymer (i.e., with no or substantially no polymer of natural origin).

The use of fully synthetic organic polymers within the context of the present invention provides an advantage over existing membranes consisting only of polymers of cellulose compounds and their derivatives. The use of fully synthetic organic polymers allows for enhanced uniformity in the preparation of the membranes, yielding more uniform experimental results, and reduces the hazards associated with membranes consisting only of polymers of cellulose compounds and their derivatives. While any suitable fully synthetic organic polymer can be used within the context of the present invention, preferred fully synthetic organic polymers include polyethersulfones; polysulfones; polyamides, including polyarylamides (aramides); polyetheramides; polyacetals; polyacrylonitrile and acrylonitrile copolymers such as poly(styrene/acrylonitrile); polyarylenesulfides; polyetherimides; polyetherketones, polyetheretherketones, and polyarylene(ether)ketone variants; polyimides; polyesters; polycarbonates; polyacrylates, including polymethacrylates, polyalkylacrylates, and the like; polystyrene; polyolefin homopolymers and copolymers such as polyethylene, polypropylene, polybutylene, and the like; halogenated polyolefins such as polyvinylchloride, polyvinylidenefluoride, polytetrafluoroethylene, and the like; thermoplastic polyurethanes; and combinations thereof. More preferably, the fully synthetic organic polymer is a polyethersulfone, polysulfone, polyamide, polyolefin, polyimide, halogenated polyolefin, or a combination thereof.

"Synthetic" polymers which are derived from chemical modification of naturally occurring substances are not "fully synthetic polymers" as that term is defined herein. Examples of such polymers of natural origin include nitrocellulose, cellulose acetate, higher acetylated cellulose products such as cellulose triacetate, cellulose propionate, cellulose butyrate, cellulose xanthate, and the like, as well as combinations thereof.

Biological Molecule

As used herein, the term "biological molecule" includes any peptide, protein, nucleic acid, derivative thereof, or combination thereof. While the biological molecule of interest can be any peptide, protein, nucleic acid, derivative thereof, or combination thereof, the biological molecule of interest is preferably a protein, nucleic acid, or a protein-nucleic acid fusion molecule; more preferably, the biological molecule of interest is a protein, DNA, or RNA.

Cellulose Compound

The cellulose compound utilized within the context of the present invention serves many functions. As previously stated, in order for a membrane to be used effectively in an immunodiagnostic or a blotting assay, the membrane's immunodiagnostic or blotting properties desirably are optimized. The membrane's signal-to-noise ratio desirably is such that the signal being emitted by the means for detecting the biological molecule of interest can be adequately detected, e.g., visualized. To that end, the cellulose compound can serve to reduce the binding of biological molecules not of interest while maintaining an acceptable level of binding of the biological molecule of interest. Such can be accomplished by exploiting the different binding constants that biological molecules have with respect to various cellulose compounds. For example, the use of cellulose compounds to reduce membrane adsorbability of proteins is well known in the art. See, generally, U.S. Pat. No. 4,968, 533 (Gsell). Furthermore, it is well known in the art that membranes which exhibit reduced protein adsorbability are even less able to adsorb nucleic acids. Also, the cellulose compound can serve to enhance the growth of microorganisms on the membrane when such a capability is desired. See, generally, U.S. Pat. No. 5,595,893 (Pometto, III et al.).

While any suitable cellulose compound, and derivative thereof, can be used within the context of the present invention, preferred cellulose compounds include nitrocellulose, ether derivatives of cellulose, ester derivatives of cellulose, xanthate derivatives of cellulose, and combinations thereof. Preferably, the ether derivative of cellulose is methylcellulose, carboxylated alkyl cellulose, or hydroxyalkylcellulose. A preferred hydroxyalkylcellulose is hydroxypropylcellulose. The preferred ester derivative of cellulose is cellulose acetate, and, preferably, the xanthate derivative of cellulose is rayon, cellophane, or viscose. More preferably, the cellulose compound is a blend of nitrocellulose and a cellulose derivative selected from the group consisting of an ether derivative of cellulose, an ester derivative of cellulose, a xanthate derivative of cellulose, and combinations thereof.

When nitrocellulose is used as either the polymer of natural origin and/or the cellulose compound, either alone or in combination with other polymers of natural origin and/or cellulose compounds, the nitrocellulose desirably is highly purified and, preferably, has a degree of nitration of from about 5% to about 14%; more preferably, the degree of nitration is from about 8% to about 12%; even more preferably, the degree of nitration is from about 11% to about 12%; and most preferably, the degree of nitration is from 11.3% to 11.8%. Furthermore, the nitrocellulose preferably has a viscosity of about 18 to about 45 cps; more preferably, the nitrocellulose has a viscosity of about 30 to about 35 cps, as measured by standard methods in a combined ethanol, toluene, ethyl acetate solvent. Lower viscosity nitrocellulose appears to provide superior membranes; however, nitrocellulose in the 30–35 cps range shows little difference over less viscous nitrocellulose and is more readily available.

It is desirable to minimize the amount of cellulose compound incorporated into the present inventive membrane in order to minimize the hazards associated therewith, but such a consideration must be viewed in light of the desire to produce a membrane with desirable immunodiagnostic and/or blotting properties, which necessarily requires the use of a cellulose compound. Thus, the cellulose compound is preferably incorporated into the membrane in a quantity minimally required to realize desirable immunodiagnostic and/or blotting properties. In other words, the cellulose compound is preferably incorporated into the membrane in a quantity which is minimally required to realize an adequate signal-to-noise ratio (e.g., up to 1 wt. % based on the overall weight of the membrane). Therefore, for example, the constituents of a membrane can constitute 1 wt. % of a cellulose compound (e.g., nitrocellulose) and 99 wt. % of a 90:10 mixture of a fully synthetic organic polymer (e.g., polyethersulfone) and a polymer of natural origin (e.g., cellulose triacetate), respectively. Alternatively, the membrane can constitute up to 2 wt. %, up to 5 wt. %, or up to 10 wt. %, or even more, cellulose compound based on the weight of the membrane.

Not only is the quantity of the cellulose compound a significant consideration, but so too is the way in which the cellulose compound is distributed in the membrane. While the cellulose compound can be distributed throughout the surface of the membrane in any suitable way, preferably, it is uniformly or substantially uniformly distributed throughout the surface of the membrane. Uniform distribution is important because if the cellulose compound is non-uniformly distributed throughout the membrane, the localized concentration of the cellulose compound will vary throughout the surface of the membrane, and, consequently, the immunodiagnostic and/or blotting properties of the membrane will be non-uniform, thereby adversely affecting performance. The distribution of the cellulose compound throughout the surface of the membrane can be such that the cellulose compound completely or substantially covers the entire surface of the membrane.

The cellulose compound can be a coating on the surface of the membrane, applied ex situ to an already formed membrane comprising the polymer solids. The cellulose compound also can be in admixture (i.e., form a blend) with the polymer solids from which a membrane comprising the admixture is formed by otherwise conventional methods (i.e., the cellulose compound is distributed in situ). Alternatively, the cellulose compound can be both a coating on the membrane and in admixture with the polymer solids forming the membrane. Also, the cellulose compound should be distributed in a quantity sufficient and in such a way so as to cause the cellulose compound to reside throughout the surface of the membrane, both on external surfaces and, if the membrane is porous, internal surfaces.

Membrane

The present inventive membrane can be either porous or non-porous. Whether the present inventive membrane is porous or non-porous is dictated by the context in which the membrane is to be used, e.g., by the sensitivity of the means used to detect the biological molecule of interest. For blotting assays which utilize more sensitive detection means, the membrane need not be porous because the biological molecule of interest can be fixed at the surface of the membrane in a quantity sufficient to allow detection. For blotting assays which utilize less sensitive detection means, it is generally preferred that the membrane be porous to allow for a larger quantity of biological molecules to be fixed to the membrane and consequently detected, e.g., to allow for the visualization of the less sensitive detection means. The desired pore rating of the membrane is a function of the size of the biological molecule that is being detected as well as the size of the detecting means (e.g., a radiolabeled oligonucleotide, an antibody, etc.). Preferably, the pore rating of the membrane is in the range of 0.1 $\mu$m–20 $\mu$m; more preferably, the pore rating is in the range of 1 $\mu$m–10 $\mu$m; even more preferably, the pore rating is in the range of 2 $\mu$m–7 $\mu$m; and most preferably, the pore rating is in the range of 3 $\mu$m–6 $\mu$m. It should be noted that when a porous membrane is desired, no coating thereof should act to significantly block the pores of the membrane. However, whereas a membrane used within the context of a blotting assay may or may not be porous, depending on considerations such as the sensitivity of the detection means, it is undesirable that such a membrane allow for the lateral diffusion of biological molecules. In contrast, membranes used within the context of immunodiagnostic assays desirably allow for the lateral diffusion of biological molecules.

The membrane also can comprise a hydrophilic compound such that the surface of said membrane is hydrophilic. Like the cellulose compound, the hydrophilic compound can exist as a coating on the membrane when the ex situ process for membrane formation is utilized; the hydrophilic compound can be in admixture with the polymer solids from which a membrane comprising the admixture is formed by traditional methods (i.e., the in situ process); or alternatively the hydrophilic compound can be both a coating on the membrane and in admixture with the polymer solids of the membrane. For purposes of economy in membrane preparation, it is preferred that, when the ex situ process is utilized to prepare the present inventive membrane, the coating solution comprising the cellulose compound should further comprise the hydrophilic compound. While any suitable hydrophilic compound can be utilized within the context of the present inventive membrane, preferred hydrophilic compounds include surfactants and polymeric wetting agents. Preferably, the surfactant is ionic; more preferably, the surfactant is anionic; even more preferably, the surfactant is a monodentate sulfonate and/or an alpha olefin sulfonate surfactant; and most preferably, the surfactant is Bioterge AS-40, manufactured by Stepan Co. The polymeric wetting agent is preferably a polyquaternary amine, and the preferred polyquaternary amines are those described in U.S. Pat. No. 5,021,160 (Wolpert) as a copolymer of 2-acrylamido-2-methyl-1-propanesulfonic acid (AMPS) and either N-(isobutoxymethyl)acrylamide (IBMA) or 2-hydroxyethyl methacrylate (HEMA).

Furthermore, following formation of the membrane, the membrane can be further modified in any suitable way in accordance with its intended use. In other words, the membrane's immunodiagnostic and/or blotting properties can be enhanced via modification of the membrane. For example, within the context of an immunodiagnostic assay, the signal-to-noise ratio of the membrane can be enhanced by attaching, to the membrane, any suitable detecting agent (e.g., antibodies which fluoresce upon binding specific antigens). Methods for attaching acceptor molecules (e.g., antibodies) to membranes are well known in the art. See, generally, U.S. Pat. No. 4,886,836 (Gsell et al.). In addition, the membrane can be cut into a particular size and/or shape or placed in housings suitable for its intended use.

The membrane can be supported or unsupported. If it is desired that the membrane be supported, any suitable support can be used within the context of the present invention, e.g., a woven or non-woven support.

Methods of Preparation

As previously stated, the present invention provides two methods of preparing membranes: (1) ex situ preparation whereby a coating is applied ex situ to a pre-formed base membrane comprising the polymer solids and (2) in situ preparation whereby the cellulose compound is admixed with the polymer solids and the admixture is used to prepare the membrane.

When utilizing the ex situ preparative method, a membrane is prepared by selecting a pre-formed base membrane comprising the polymer solids and then uniformly coating the base membrane with a coating solution that comprises the cellulose compound and a cellulose dissolving agent.

The cellulose dissolving agent is a solvent with respect to the cellulose compound but is a non-solvent with respect to the selected pre-formed base membrane. By "non-solvent" it is meant that the cellulose dissolving agent is either a poor solvent with respect to the pre-formed base membrane, or, alternatively, a solvent which has absolutely no effect on the performance of the base membrane. A poor solvent is one which may cause the base membrane to swell but not dissolve or one which, under the process conditions (e.g., solvent concentration, time of contact, temperature, etc.), causes no significant or substantial amount of the base membrane to dissolve. The cellulose dissolving agent used within the context of the present invention is chosen so that the performance of the base membrane is not significantly or substantially effected. While any suitable cellulose dissolving agent can be used within the context of the present invention, preferred cellulose dissolving agents include methylacetate and methanol. The concentration of cellulose compound dissolved in the cellulose dissolving agent should be such that, if the membrane to be coated is porous, the cellulose compound will not substantially obscure the pores. Preferably the concentration of cellulose compound in the coating solution is from about 0.1 wt. % to about 5 wt. %; more preferably, from about 0.2 wt. % to about 2 wt. %; and most preferably, from about 0.3 wt. % to about 1 wt. %.

After the base membrane is uniformly coated with the coating solution, the coating is cured by any suitable method, e.g., traditional methods well known in the art. It is important to note that the coating solution can contain other materials which may enhance the properties of the membrane. For example, the coating solution can contain a hydrophilic compound which renders the resulting membrane hydrophilic, as previously discussed.

When utilizing the in situ preparative method, a membrane is prepared by selecting polymer solids and admixing the polymer solids with the cellulose compound such that the cellulose compound is uniformly distributed throughout the surface of the resulting membrane. After admixing the cellulose compound with the polymer solids, the membrane is formed through any suitable method, e.g., conventional methods which are well known in the art, particularly through a coating process. See, generally, U.S. Pat. No. 4,707,266. Of course, the membrane prepared by the in situ preparative method can be utilized as a base membrane in the ex situ preparative method wherein it may undergo coating. Furthermore, the admixture can contain other materials which may enhance the properties of the membrane. For example, the admixture can contain a hydrophilic compound which renders the membrane hydrophilic, as previously discussed.

Methods for forming membranes, whether by virtue of the ex situ or in situ process, are well known in the art. Such methods for membrane formation include but are not limited to irradiative polymerization of unsaturated monomers in a solvent in which the monomer is soluble but the polymer is not, as disclosed in U.S. Pat. No. 4,466,931; graft-polymerization to form a gel followed by shearing to form a thixotropic mixture which may be cast to form a membrane, as disclosed in U.S. Pat. No. 4,374,232; thermally induced precipitation; membrane coagulation due to solvent leaching, as disclosed in EP 0 036 947; membrane coagulation in a humid atmosphere, as illustrated by U.S. Pat. Nos. 4,900,499, 4,964,490, and 5,108,607; and membrane casting, as disclosed in U.S. Pat. Nos. 3,876,738, 4,340,479, 4,473,474, 4,673,504, 4,708,803, and 4,711,793. Other patents and publications which illustrate the preparation of membranes include U.S. Pat. No. 4,629,563, EP 0 036 315, EP 0 037 185, EP 0 165 077, DE 26 51 818, DE 28 29 630, DE 33 27 638, DE 33 42 824, DE 37 01 633, GB 1 295 585, GB 1 473 857, and GB 1 495 887.

In either the ex situ or in situ process, the membrane produced therefrom can be supported on a suitable support, e.g., a woven or non-woven support. For ex situ membranes, the finished membrane can be laminated to a support by any suitable means, e.g., by way of direct thermal lamination or by way of a suitable adhesive. For in situ membranes, the membrane can be cast on the desired support. It is important that if a porous membrane is desired, then the means used to attach the support to the membrane not cause the membrane to significantly lose its porosity.

Both the ex situ and in situ preparative methods can further comprise steps involving the recovery of a membrane and the testing of the immunodiagnostic and/or blotting properties of the recovered membrane such that the preparative method can be adjusted or optimized in response to the test's results in order to alter or enhance the immunodiagnostic and/or blotting properties of the membrane. In other words, the preparative method can include a feedback mechanism whereby the membrane's immunodiagnostic and/or blotting properties are tested and, in response to the test's results, the process conditions of the preparative method are adjusted so as to yield a membrane with altered or enhanced properties.

As previously stated, optimal immunodiagnostic and/or blotting properties include a membrane's ability to be safely used in a laboratory environment (e.g., the membrane is not flammable or explosive), its ability to be uniformly manufactured in order to yield consistent experimental results, its hydrophilicity, and its ability to strongly bind biological molecules of interest while weakly binding biological molecules not of interest (i.e., the membrane is capable of a high signal-to-noise ratio). Therefore, any membrane prepared by the foregoing preparative methods can be tested for its immunodiagnostic and/or blotting properties, and the process conditions of the preparative method can be adjusted in response to the test so as to enhance or otherwise alter the immunodiagnostic and/or blotting properties of the membrane produced therefrom.

The suitability of the present inventive membranes for any particular immunoassay and/or blotting method, of course, is determined on a case by case basis. Such testing is routine to those skilled in the art and is practiced, for example, for each immunodiagnostic and/or blotting product both prior to commercialization as well as for quality control during production.

Methods of Use

The present inventive membrane can be used within the context of any application where it is desired to detect a biological molecule of interest. While the membrane can be used in any suitable way, preferably, the method for using the present inventive membrane comprises (a) contacting the membrane with a fluid comprising the biological molecule of interest and (b) detecting the biological molecule of interest on the membrane. Alternatively, the method comprises (a) contacting the membrane with a fluid comprising the biological molecule of interest, (b) allowing the fluid to laterally diffuse through the membrane, and (c) detecting the biological molecule of interest on the membrane.

Immunodiagnostic and Blotting Assay Kits

Another embodiment of the present invention is a kit which can be used for immunodiagnostic and/or blotting assays.

The immunodiagnostic assay kit comprises a membrane and a means for infecting a biological molecule of interest. While any suitable detection means can be utilized within the context of the present invention, the detection means is preferably a dye, an interchelating agent, a fluorescent probe, or a radioactive probe.

The blotting assay kit comprises a membrane and a blotting solution. While the blotting solution can be any solution utilized within the context of a blotting assay, the blotting solution is preferably a pH-buffering solution or a solution with a specific ionic concentration.

EXAMPLES

The following examples further illustrate the present invention but, of course, should not be construed as in any way limiting its scope.

In Examples 1–4, a commercially available, hydrophilic, polyethersulfone, microporous membrane having a nominal pore size of 5 $\mu$m, available from Gelman Sciences, Inc., as Supor® 5000, was used to prepare several lateral flow microporous membranes suitable for use in immunoassays. The membrane, in each case, was used dry.

Example 1

A coating solution of nitrocellulose was prepared at room temperature. Hercules RS and SS nitrocellulose resins (5 g) having degrees of nitration of 12% and 11%, respectively, were mixed with methylacetate (995 g) to yield a coating solution with an average degree of nitration between 11.3% and 11.8%. The mixture was agitated for 4 hours, and a clear solution was obtained. Samples of dry, hydrophilic, polyethersulfone membrane with a 5 $\mu$m nominal pore rating were dipped into the coating solution and allowed to dry at room temperature. The membranes were stored at room temperature for use in Example 3.

Example 2

A coating solution of nitrocellulose (5 g) and methanol (995 g) was prepared at room temperature. The mixture was agitated for 4 hours, and a clear solution was obtained. Samples of dry, hydrophilic, polyethersulfone membrane with a 5 $\mu$m nominal pore rating were dipped into the coating solution and allowed to dry at room temperature. The membranes were stored at room temperature for use in Example 3.

Example 3

Bioterge AS-40 (1 g) (available from Stepan Co.) was mixed with deionized water (999 g), and the mixture was agitated for 4 hours. A clear, slightly yellow solution was obtained. Samples of the membranes prepared in Examples 1 and 2 were dipped into the solution and dried at 60° F. (15.6° C.) for 1 hour. The membranes were hydrophilic after treatment and were stored at room temperature as suitable for use in immunodiagnostic assays.

Example 4

A solution of Bioterge AS-40 (1 g), nitrocellulose (5 g), and methanol (994 g) was prepared. Samples of dry, hydrophilic, polyethersulfone membranes with a 5 $\mu$m nominal pore rating were dipped into the solution and allowed to dry at room temperature. The membranes were stored at room temperature and were suitable for use in immunodiagnostic assays.

Example 5

This example illustrates in situ membrane formation. An admixture was prepared by dissolving 6.8 wt. % polyethersulfone polymer in 9.4 wt. % dimethylformamide, 65.8 wt. % polyethylene glycol 400, 0.4 wt. % polyvinylpyrollidone K90, 9.8 wt. % N-methylpyrollidone, and 1.6 wt. % Aquazol 500 (available from Polymer Chemistry Innovations), to which was added 0.2 wt. % nitrocellulose and 0.2 wt. % Bioterge AS-40. The balance of the admixture was water. The admixture was applied to a glass plate at a thickness of about 18 mil (457.2 $\mu$m) and placed in a low air velocity humid environment until the composition became cloudy. The resulting membrane was then dried in air to form a membrane with a 5 $\mu$m nominal pore rating. The membrane was dipped in surfactant and dried to form a hydrophilic membrane suitable for immunoassay use.

Example 6

A microporous lateral flow membrane as prepared in Example 4 was compared to a commercial nitrocellulose membrane of similar pore size (available from Millipore Corp., Bedford, Mass.). The test protocol utilized rabbit IgG antigen, mouse anti-rabbit IgG conjugate, mouse anti-rabbit IgG ($\gamma$-specific) as a capture line, and goat anti-mouse IgG as a control line, as previously indicated.

In the test protocol utilized in the present example, colloidal gold conjugates, such as those disclosed in EP 0 250 137 were utilized. The gold colloids were prepared by adding 4 ml of 1% gold chloride to 200 ml boiling water to which was added 12 ml of 1% trisodium citrate. The solution was mixed well. The gold colloid thus produced contained 30–40 nm gold beads which displayed a wine-red color. The colloid can be stored in the dark at room temperature.

To prepare the gold conjugate, 1 ml of colloidal gold was added to a microcentrifuge tube, and 25 $\mu$l of 1 mg/ml dialyzed mouse anti-rabbit IgG (Pierce 31213) and 100 μl of 20 mM borax solution were added and left to stand for 1 hour at room temperature. Next, 100 μl of 1% BSA/20 mM borax solution is added to the tube, at which time the tube was centrifuged at 15 k for 50 minutes. The supernatant was withdrawn, and the pellet was resuspended in 1 ml of 0.1% BSA/2 mM borax buffer. The suspension was again centrifuged, and the obtained pellet was resuspended in 250 μl of the buffer solution. The gold-conjugated antibody was stored at 4° C. prior to use.

The gold conjugated antibody was diluted 1:4 with 100 mM Tris pH=7 containing 10% BSA, 0.1% Tween 20, and 10% sucrose, and applied to a glass conjugate pad by dipping, followed by drying at 58° C. for 30 minutes. The membranes to be tested were sprayed with the appropriate solutions with the control line and test line set at 0.5 mm line width and sprayed twice at a loading of 0.2 μl/cm. The assembled strip constituted, in linear order, a sample application pad, a conjugate pad with mouse anti-rabbit IgG conjugate, a membrane having both a test line (mouse anti-rabbit IgG (γ-specific)/1 mg/ml) and a control line (goat anti-mouse IgG (2 mg/ml), and an absorption pad.

Samples of 200 μl of rabbit IgG antigen were applied to the sample application pad and allowed to migrate through the conjugate pad and into the membrane. The antigen was detected at the test line of the membrane. The results are presented in the table below:

| Membrane | Reaction Time (Minutes) | Sensitivity | Signal Appearance |
| --- | --- | --- | --- |
| Present Invention | 2.5 | 50 ng/ml | Good |
| Comparative | 3.0 | 50 ng/ml | Good |

The results indicate that the present inventive membrane exhibited a faster response time than the nitrocellulose-based membrane while being equivalent in sensitivity and signal appearance. In addition, the present inventive membrane was far stronger and far less flammable.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A porous membrane comprising (a) polymer solids comprising 60 wt. % or more of a fully synthetic organic polymer and optionally about 40 wt % or less of a polymer of natural origin and (b) a nitrocellulose compound which allows for the detection of a biological molecule of interest, wherein said nitrocellulose compound is uniformly distributed throughout the surface of said membrane, and wherein said membrane has a pore rating of about 0.1–20 μm.

2. The membrane of claim 1, wherein said polymer solids comprise 80 wt. % or more of a fully synthetic organic polymer and optionally about 20 wt. % or less of a polymer of natural origin.

3. The membrane of claim 1, wherein said nitrocellulose is a coating on the surface of said membrane.

4. The membrane of claim 1, wherein said nitrocellulose is in admixture with said polymer solids.

5. The membrane of claim 1, further comprising a hydrophilic compound such that the surface of said membrane is hydrophilic.

6. The membrane of claim 5, wherein said hydrophilic compound is a surfactant.

7. The membrane of claim 1, further comprising a cellulose derivative selected from the group consisting of an ether derivative of cellulose, an ester derivative of cellulose, a xanthate derivative of cellulose, and combinations thereof.

8. The membrane of claim 7, wherein said ether derivative of cellulose is selected from the group consisting of methylcellulose, carboxylated alkyl cellulose, and hydroxyalkylcellulose, said ester derivative of cellulose is cellulose acetate, and said xanthate derivative of cellulose is selected from the group consisting of rayon, cellophane, and viscose.

9. The membrane of claim 8, wherein said hydroxyalkylcellulose is hydroxypropylcellulose.

10. The membrane of claim 7, wherein said nitrocellulose compound is a coating on the surface of said membrane.

11. The membrane of claim 7, wherein said fully synthetic organic polymer is selected from the group consisting of polyethersulfone, polysulfone, polyamide, polyolefin, polyimide, halogenated polyolefins, and combinations thereof.

12. The membrane of claim 7, further comprising a hydrophilic compound such that the surface of said membrane is hydrophilic.

13. The membrane of claim 7, wherein said nitrocellulose compound is in admixture with said polymer solids.

14. The membrane of claim 1, wherein said nitrocellulose compound is a coating on the surface of said membrane and in admixture with said polymer solids.

15. A porous membrane comprising (a) polymer solids comprising 60 wt. % or more of a fully synthetic organic polymer and optionally about 40 wt. % or less of a polymer of natural origin and (b) a nitrocellulose compound, wherein said nitrocellulose compound is in admixture with said polymer solids, and wherein said membrane has a pore rating of about 0.1–20 μm.

16. A method of preparing a porous membrane comprising (a) selecting a base membrane comprising polymer solids, said polymer solids comprising 60 wt. % or more of a fully synthetic organic polymer and optionally about 40 wt. % or less of a polymer of natural origin, and (b) uniformly coating said base membrane with a coating solution, said coating solution comprising a nitrocellulose compound which allows for the detection of a biological molecule of interest and a nitrocellulose dissolving agent which is a solvent for said nitrocellulose compound and is a non-solvent for said base membrane, to provide a porous membrane wherein said nitrocellulose compound is uniformly distributed throughout the surface of said membrane, and wherein said membrane has a pore rating of about 0.1–20 μm.

17. The method of claim 16, wherein said polymer solids comprise 80 wt. % or more of a fully synthetic organic polymer and optionally about 20 wt. % or less of a polymer of natural origin.

18. The method of claim 16, wherein said coating solution further comprises a hydrophilic compound such that the surface of said membrane is hydrophilic.

19. The method of claim 16, wherein said coating solution further comprises a cellulose derivative selected from the group consisting of an ether derivative of cellulose, an ester derivative of cellulose, a xanthate derivative of cellulose, and combinations thereof.

20. The method of claim 19, wherein said ether derivative of cellulose is selected from the group consisting of methylcellulose, carboxylated alkyl cellulose, and hydroxyalkylcellulose, said ester derivative of cellulose is cellulose acetate, and said xanthate derivative of cellulose is selected from the group consisting of rayon, cellophane, and viscose.

21. The method of claim 20, wherein said hydroxyalkylcellulose is hydroxypropylcellulose.

22. The method of claim 19, wherein said fully synthetic organic polymer is selected from the group consisting of polyethersulfone, polysulfone, polyamide, polyolefin, polyimide, polyvinylidenefluoride, and combinations thereof.

23. The method of claim 19, wherein said coating solution further comprises a hydrophilic compound such that the surface of said membrane is hydrophilic.

24. A method of preparing a porous membrane comprising (a) admixing (i) polymer solids comprising 60 wt. % or more of a fully synthetic organic polymer and optionally about 40 wt. % or less of a polymer of natural origin and (ii) a nitrocellulose compound, and (b) casting the admixture of step (a) to prepare a membrane wherein said nitrocellulose compound is uniformly distributed throughout the surface of said membrane, and wherein said membrane has a pore rating of about 0.1–20 $\mu$m.

25. The method of claim 24, wherein said polymer solids comprise 80 wt. % or more of a fully synthetic organic polymer and optionally about 20 wt. % or less of a polymer of natural origin.

26. The method of claim 24, wherein the surface of said membrane is hydrophilic.

27. The method of claim 24, further comprising admixing, with said polymer solids and said nitrocellulose compound, a cellulose derivative selected from the group consisting of an ether derivative of cellulose, an ester derivative of cellulose, a xanthate derivative of cellulose, and combinations thereof.

28. The method of claim 27, wherein said ether derivative of cellulose is selected from the group consisting of methylcellulose, carboxylated alkyl cellulose, and hydroxyalkylcellulose, said ester derivative of cellulose is cellulose acetate, and said xanthate derivative of cellulose is selected from the group consisting of rayon, cellophane, and viscose.

29. The method of claim 28, wherein said hydroxyalkylcellulose is hydroxypropylcellulose.

30. The method of claim 24, wherein said fully synthetic organic polymer is selected from the group consisting of polyethersulfone, polysulfone, polyamide, polyolefin, polyimide, polyvinylidenefluoride, and combinations thereof.

31. The method of claim 24, wherein the surface of said membrane is hydrophilic.

32. A method of using the membrane of claim 1 to detect a biological molecule of interest comprising (a) contacting said membrane with a fluid comprising said biological molecule of interest and (b) detecting said biological molecule of interest on said membrane.

33. An immunodiagnostic assay kit comprising the membrane of claim 1 and a means for detecting a biological molecule of interest.

34. A blotting assay kit comprising the membrane of claim 1 and a blotting solution.

* * * * *